United States Patent
Berger et al.

(10) Patent No.: US 9,107,767 B2
(45) Date of Patent: Aug. 18, 2015

(54) INTERVERTEBRAL CAGE WITH ANTERIOR FIXATION AND STABILIZATION

(71) Applicant: DePuy Synthes Products, LLC, Raynham, MA (US)

(72) Inventors: Roger Berger, Oberdorf (CH); Ryan Vanleeuwen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 110 days.

(21) Appl. No.: 13/742,470

(22) Filed: Jan. 16, 2013

(65) Prior Publication Data

US 2014/0200669 A1    Jul. 17, 2014

(51) Int. Cl.
| | | |
|---|---|---|
| *A61F 2/44* | (2006.01) | |
| *A61B 17/064* | (2006.01) | |
| *A61B 17/86* | (2006.01) | |
| *A61F 2/28* | (2006.01) | |
| *A61F 2/30* | (2006.01) | |

(52) U.S. Cl.
CPC ............... *A61F 2/447* (2013.01); *A61B 17/064* (2013.01); *A61B 17/86* (2013.01); *A61F 2002/2835* (2013.01); *A61F 2002/30383* (2013.01); *A61F 2002/30576* (2013.01); *A61F 2002/30904* (2013.01)

(58) Field of Classification Search
CPC .................................... A61F 2/44; A61F 2/447
USPC .............................. 623/17.11–17.16; 606/281
See application file for complete search history.

(56) References Cited

U.S. PATENT DOCUMENTS

| | | | |
|---|---|---|---|
| 7,112,222 B2 * | 9/2006 | Fraser et al. ................ | 623/17.11 |
| 7,658,766 B2 | 2/2010 | Melkent et al. | |
| D623,745 S | 9/2010 | Kay et al. | |
| D623,751 S | 9/2010 | Weiman | |
| 7,905,922 B2 | 3/2011 | Bergeron | |
| 8,062,335 B1 | 11/2011 | McAfee | |
| 8,100,875 B2 | 1/2012 | Cline et al. | |
| 8,591,588 B2 | 11/2013 | Fraser et al. | |
| 2005/0071008 A1 * | 3/2005 | Kirschman ................ | 623/17.11 |
| 2007/0191954 A1 | 8/2007 | Hansell et al. | |
| 2008/0154376 A1 | 6/2008 | Bergeron | |
| 2008/0300634 A1 * | 12/2008 | Gray .............................. | 606/280 |
| 2009/0054987 A1 | 2/2009 | Chin et al. | |
| 2009/0326580 A1 * | 12/2009 | Anderson et al. ............. | 606/246 |
| 2010/0145453 A1 | 6/2010 | Kirschman | |
| 2010/0249937 A1 | 9/2010 | Blain et al. | |
| 2010/0274358 A1 * | 10/2010 | Mueller et al. ............. | 623/17.16 |
| 2011/0082550 A1 * | 4/2011 | Yeh ............................. | 623/17.11 |
| 2011/0093074 A1 | 4/2011 | Glerum et al. | |

(Continued)

FOREIGN PATENT DOCUMENTS

| | | |
|---|---|---|
| CN | 2875347 | 3/2007 |
| CN | 201085669 | 7/2008 |

(Continued)

*Primary Examiner* — Matthew Lawson
*Assistant Examiner* — Si Ming Lee
(74) *Attorney, Agent, or Firm* — Nutter McClennen & Fish LLP

(57) ABSTRACT

A spinal implant. The spinal implant includes a spacer having an upper surface for contacting a superior vertebral body, a lower surface for contacting an inferior vertebral body, a first insertion end portion, and a second end portion opposite the first insertion end portion; a fixation frame coupled to the second end portion of the spacer and including a bridge portion oriented substantially coplanar with the spacer and at least one arm extending from the bridge portion; and at least one fixation element having a first insertion end for penetrating the superior or inferior vertebral bodies and a second end coupled to the at least one arm of the fixation frame.

22 Claims, 13 Drawing Sheets

(56) References Cited

U.S. PATENT DOCUMENTS

2011/0118840 A1 5/2011 Huntsman et al.
2011/0251689 A1 10/2011 Seifert et al.

FOREIGN PATENT DOCUMENTS

| | | |
|---|---|---|
| CN | 201085671 | 7/2008 |
| EP | 2361573 | 8/2011 |
| KR | 20040017780 | 2/2004 |
| WO | 0180785 | 11/2001 |
| WO | 2007098288 | 8/2007 |
| WO | 2009/091775 A2 | 7/2009 |
| WO | 2010028095 | 3/2010 |
| WO | 2010054181 | 5/2010 |
| WO | 2010079993 | 7/2010 |
| WO | 2011130329 | 10/2011 |

* cited by examiner

INTERVERTEBRAL CAGE WITH ANTERIOR FIXATION AND STABILIZATION

TECHNICAL FIELD

The present invention relates generally to spinal implants and, in particular, to spinal implants with a spacer and a fixation frame having a zero profile design.

BACKGROUND OF THE INVENTION

Injury or advancing age can lead to degenerative changes in the bones, discs, joints, and ligaments of the spine, producing pain and instability. For example, spine instability may result from causes such as fracture, scoliosis, and spondylolisthesis, where one or more vertebrae moves relative to the other vertebrae. Spinal fusion is a surgical technique used to treat conditions where the spine exhibits instability by fusing together two or more vertebrae of the spinal column in order to eliminate the motion between the fused vertebrae.

The use of bone plate and bone screw fixation systems for treating injuries to bones is well established. In most instances, a bone plate may be positioned over and surrounding the bone injury area and secured to the bone. The bone plate may be secured to the bone by bone screws inserted through holes in the bone plate and into the bone itself. Intervertebral implants including interbody spacer portions and mechanically coupled plate portions can restore disc height, allow fusion to occur between the adjacent vertebral bodies, and provide stable fixation during healing. There remains a need, however, for improved devices for treating spinal instability. In particular, implants resting on the midline of the vertebrae or extending beyond the anterior face of the vertebrae can cause problems, such as irritation of the esophagus.

SUMMARY OF THE INVENTION

To meet these and other needs, and in view of its purposes, the present invention provides for spinal implants especially suitable for applications in the cervical, thoracic, and lumbar spine. The implant may include a zero profile design based on the selection of a fixation frame as described in this document so that the spacer portion is either flush or recessed with respect to the midline of the vertebral body.

In one embodiment, the present invention provides an implant for insertion into an intervertebral disc space between superior and inferior vertebral bodies. The implant includes a spacer having an upper surface for contacting the superior vertebral body, a lower surface for contacting the inferior vertebral body, a first insertion end portion, and a second end portion opposite the first insertion end portion. The implant also includes a fixation frame coupled to the second end portion of the spacer. The fixation frame includes a bridge portion oriented substantially coplanar with the spacer and at least one arm extending (e.g., transversely) from the bridge portion. In addition, at least one fixation element includes a first insertion end for penetrating the superior or inferior vertebral bodies and a second end coupled to at least one arm of the fixation frame.

The fixation frame may be constructed to have an H-shaped configuration. For example, a first arm may extend transversely in a first direction from a first end of the bridge portion, a second arm may extend transversely in a second direction opposite to the first direction from the first end of the bridge portion, a third arm may extend transversely in the first direction from a second end of the bridge portion, and a fourth arm may extend transversely in the second direction opposite to the first direction from the second end of the bridge portion.

The implant may be a zero profile implant. For example, the bridge portion may include a center point or center region that is substantially flush with or at least partially recessed from an anterior surface of the superior and/or inferior vertebral bodies at their respective midlines. In other words, the configuration of the implant (e.g., the H-shaped design) may be zero profile in that the portion of the implant (e.g., the bridge portion and/or the spacer) that sits on the bone does not contact the bone midline near the anterior face or surface of the superior and inferior vertebral bodies. This configuration reduces the risk of esophageal irritation.

The fixation elements, such as screws, pins, blades, staples, and the like, may be permanently affixed to the fixation frame (e.g., at the ends of the plurality of arms) such that the fixation frame and spacer are fixed prior to surgery. In the alternative, the fixation elements may be pressed into the vertebral bodies via one or more holes or openings extending through the fixation frame, which allows the fixation frame and spacer to be fixed after being placed between the vertebrae (i.e., after surgical implantation).

In another embodiment, the present invention provides an implant having an H-shaped fixation frame for insertion into an intervertebral disc space between superior and inferior vertebral bodies. The implant includes a spacer having an upper surface for contacting the superior vertebral body, a lower surface for contacting the inferior vertebral body, a first insertion end portion, a second end portion opposite the first insertion end portion, a first lateral side portion, and a second lateral side portion. The H-shaped fixation frame includes a bridge portion having a first end and a second end and a plurality of arms each having a first end coupled to the bridge portion and a second end extending from the bridge portion. The bridge portion is oriented substantially coplanar with the spacer and is coupled to the second end portion of the spacer. The plurality of arms may include a first arm extending transversely in a first direction from the first end of the bridge portion, a second arm extending transversely in a second direction opposite to the first direction from the first end of the bridge portion, a third arm extending transversely in the first direction from the second end of the bridge portion, and a fourth arm extending transversely in the second direction opposite to the first direction from the second end of the bridge portion. A plurality of fixation elements may be provided each having a first insertion end for penetrating the superior or inferior vertebral bodies and a second end coupled proximate to the second end of each of the arms of the fixation frame.

In order to achieve the zero profile design and depending on the vertebral body at issue (e.g., the anatomy of the patient), a ratio of the width of the implant relative to the height of the implant (e.g., determined by the length of the arms) and/or a ratio of the spacing of the arms (e.g., a distance between the arms) relative to the height of the implant may be selected. For example, the ratio of the width to the height may range from about 0.5 to 1.5 and the ratio of the distance between the aims to the height may range from about 0.3 to 1.2.

In addition, the bridge portion of the fixation frame may be designed and configured to provide for the zero profile design. For example, the bridge portion may be U-shaped or V-shaped. The arms may be positioned along a single vertical plane, for example, and at least a central region of the bridge portion may be recessed a distance relative to the plurality of arms (e.g., forming a concave portion between the vertebral bodies which may be filled with bone-growth materials).

The spacer may be coupled to the fixation frame, for example, via a recess in the second end portion of the spacer sized and configured to receive at least a portion of the bridge portion of the fixation frame. In addition, the bridge portion may comprise a post (e.g., centrally located) and the second end portion of the spacer may include an opening sized to receive the post. The spacer and the fixation frame may be comprised of separate elements or may form a single contiguous piece of material.

In yet another embodiment, the present invention provides a kit comprising a plurality of implants of different sizes and dimensions. For example, the kit may include implants having arms of different lengths and varying distances between the arms suitable for the vertebral body to be operated on and to achieve the zero profile design.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

The present invention provides for an implant including a spacer, a fixation frame, and one or more fixation elements for insertion into an intervertebral disc space and fixation to superior and inferior vertebral bodies. The implant may be a zero or low profile implant. As used in this document, the term "zero profile" means the entire implant or a portion of the implant (e.g., the bridge portion of the fixation frame) does not extend beyond the anterior face of the vertebral body at the midline of the vertebral body. For example, the bridge portion may include a center point or center region that is substantially flush with or at least partially recessed from an anterior face or surface at the midlines of the superior and/or inferior vertebral bodies. In other words, the configuration of the implant (e.g., the H-shaped design) may be zero profile in that the portion of the implant (e.g., the bridge portion and/or the spacer) that sits on the bone may not contact the bone midline at or near the anterior face or surface of the superior and inferior vertebral bodies. Providing for a zero profile implant, as described in this document, may help to reduce the risk of irritation to the esophagus.

Figure 2:
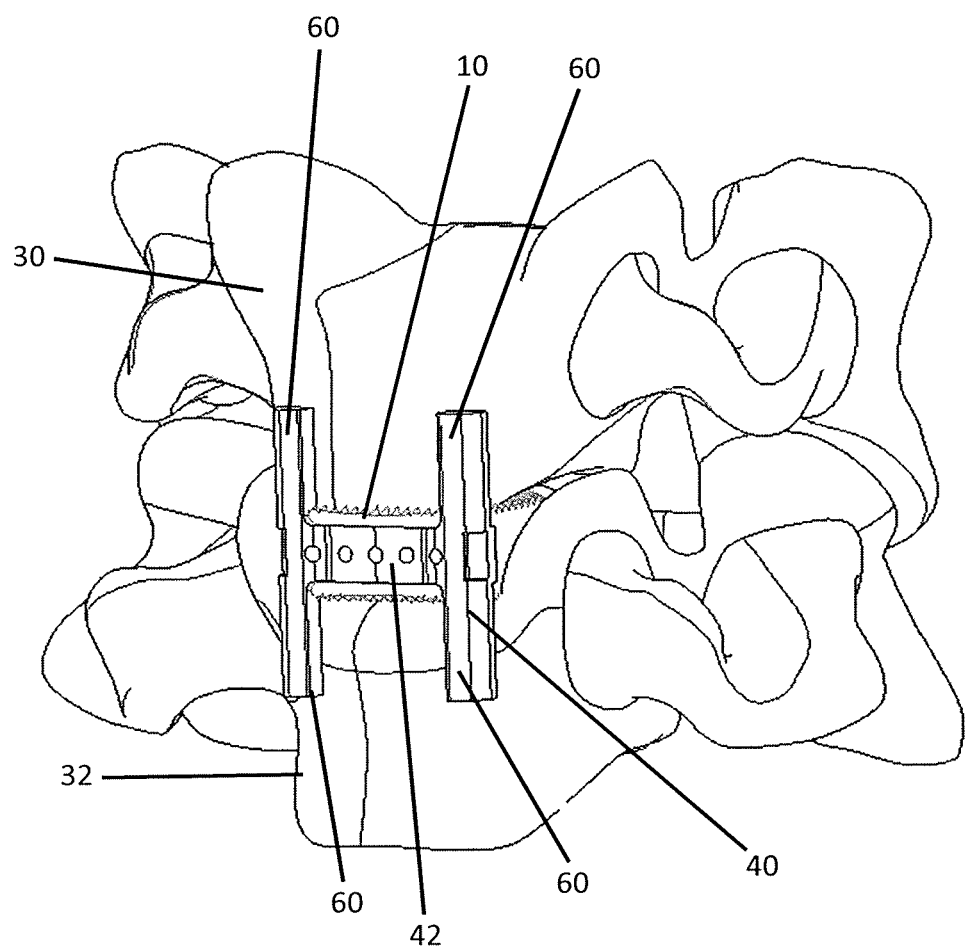
FIG. 2 shows a perspective view of the implant of FIG. 1 positioned in and affixed to the vertebral disc space.
Figure 3:
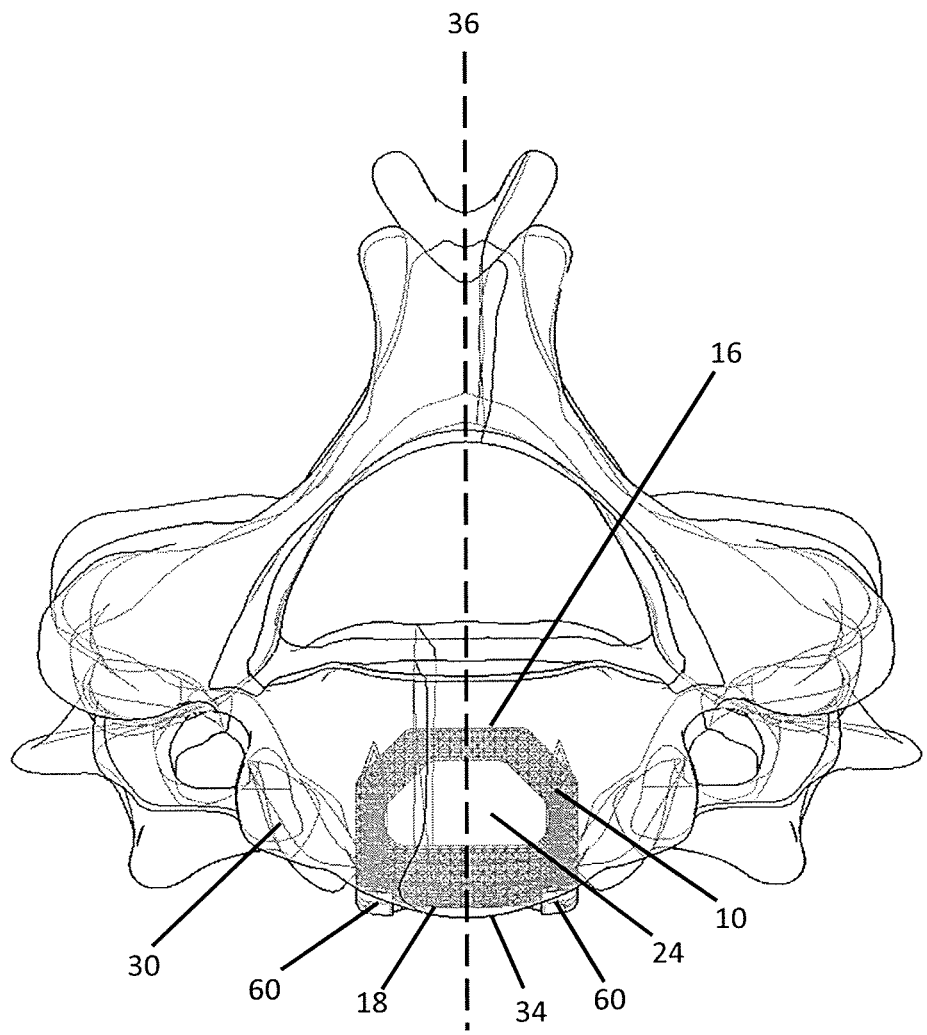
FIG. 3 is a cranial-caudal view of the implant of FIG. 1 positioned in and affixed to the vertebral disc space.
Figure 4:
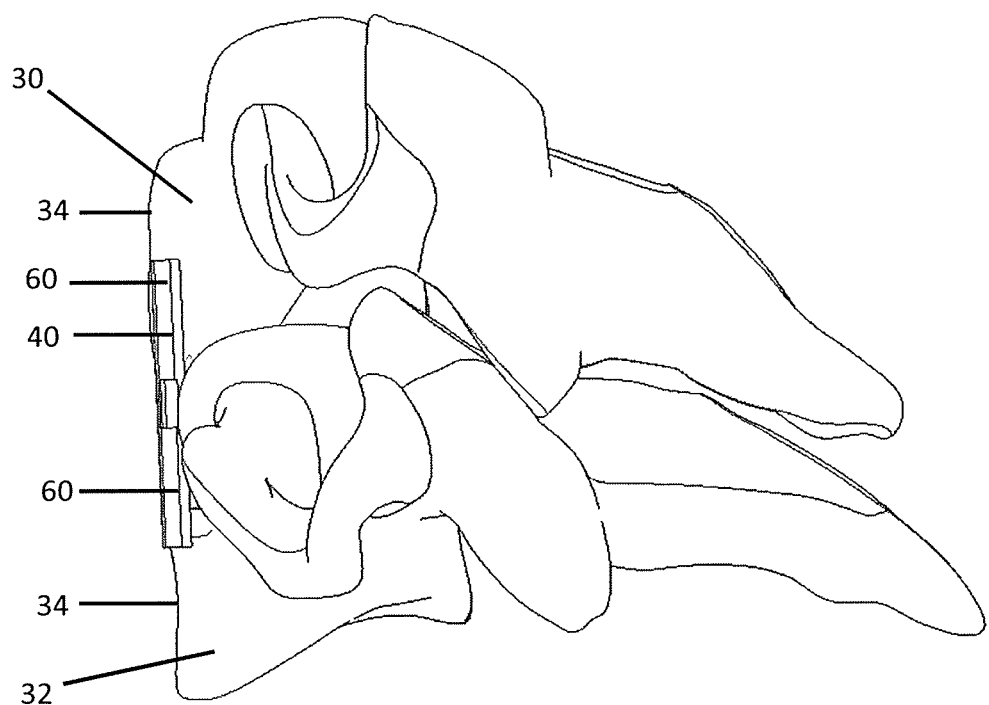
FIG. 4 depicts a lateral view of the implant of FIG. 1 positioned in and affixed to the vertebral disc space.

The implant may be inserted or implanted into an intervertebral disc space between superior and inferior vertebral bodies. As would be well known by one of ordinary skill in the art, the vertebral column includes a series of alternating vertebrae and fibrous discs that provide axial support and movement for the body. Referring now to the drawing, in which like reference numbers refer to like elements throughout the various figures that comprise the drawing, FIGS. 2-4 depict two adjacent vertebral bodies or vertebrae including a superior vertebral body 30 and an inferior vertebral body 32. In particular, FIG. 2 shows a perspective view, FIG. 3 is a cranial-caudal view, and FIG. 4 depicts a lateral view of the superior and inferior vertebral bodies 30, 32.

Spacer

Figure 1:
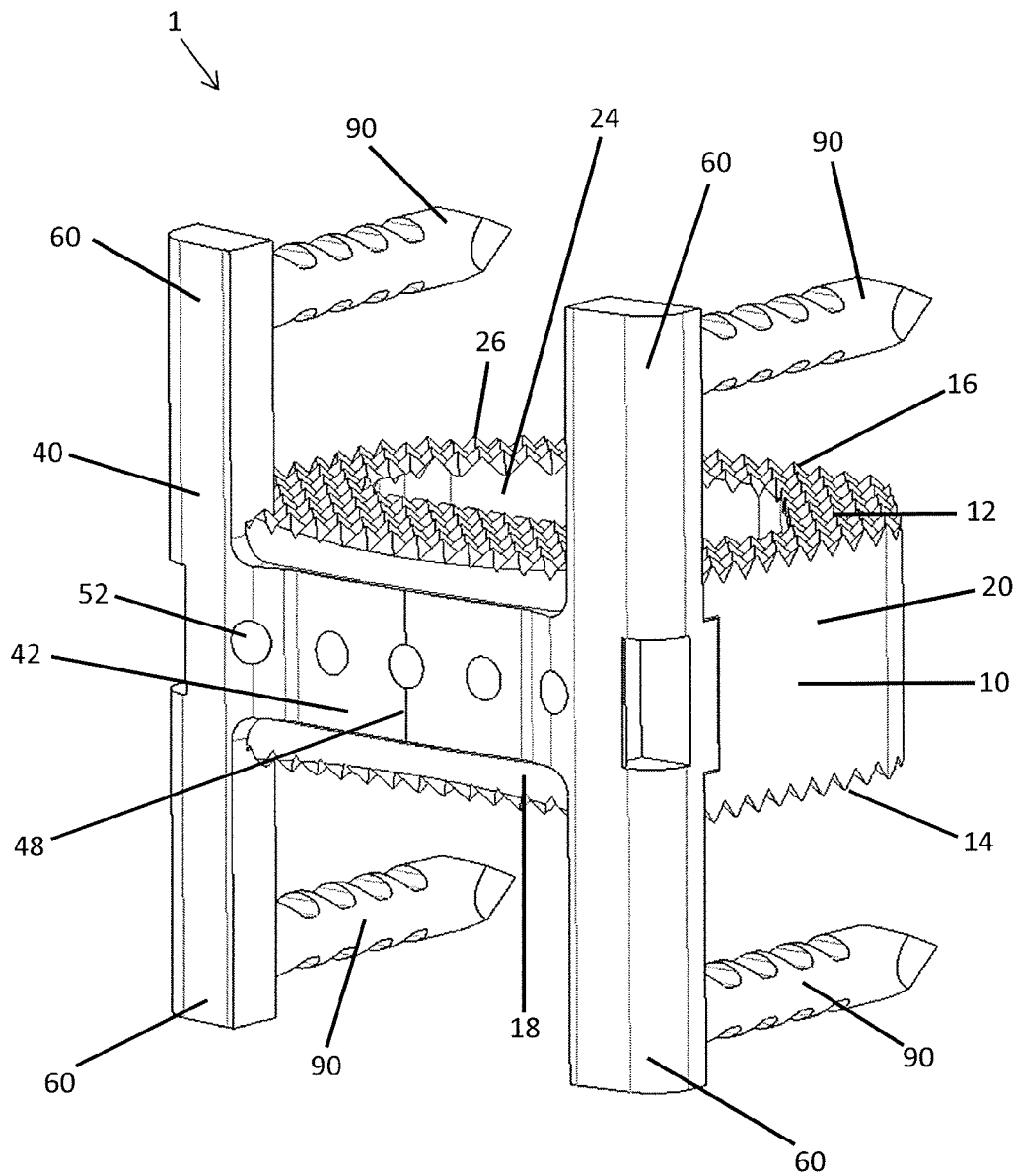
FIG. 1 shows a perspective view of one embodiment of the present invention where the implant includes a spacer, H-shaped fixation frame, and fixation elements.
Figure 5:
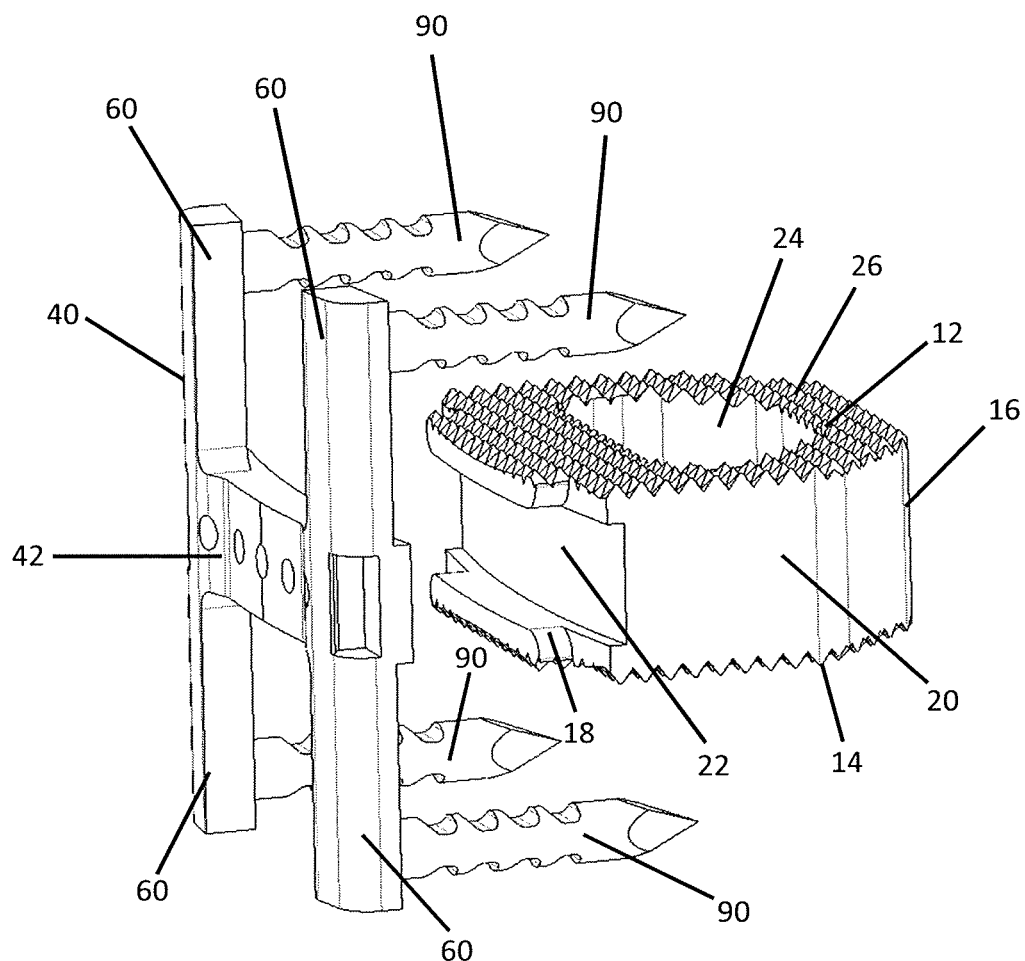
FIG. 5 shows an exploded view of the implant shown in FIG. 1.

As best seen in FIGS. 1 and 5, the implant 1 has a spacer 10. According to an embodiment of the present invention, the spacer 10 may include an upper surface 12, a lower surface 14, a first insertion end portion 16, a second end portion 18 (e.g., back end) opposite to the first insertion end portion 16, and first and second lateral side portions 20. The spacer 10 is configured and dimensioned for insertion between adjacent vertebral bodies 30, 32.

The upper and lower surfaces 12, 14 can be configured for facing the superior and inferior vertebral bodies 30, 32 adjacent to an implantation site. Thus, the upper surface 12 may contact the superior vertebral body 30 and the lower surface 14 may contact the inferior vertebral body 32. The spacer 10 may comprise any structure, for example, configured to maintain a separation and resist compression between the two adjacent vertebral bodies 30, 32. The relative configuration of the upper surface 12 and the lower surface 14 can vary, depending upon the relative position desired between the two adjacent vertebrae 30, 32, the anatomical shape of the vertebrae, ease of insertion of the implant, and other factors. For example, if a neutral vertical alignment is desired between two vertebrae 30, 32, the upper and lower surfaces 12, 14 may have generally parallel, horizontal planar orientations. In the alternative, the upper surface 12, the lower surface 14, or both surfaces 12, 14 of the spacer 10 in the implant construct may have a curved or tapered surface to help provide the proper shape to the spine and to adapt to the anatomy. The particular surface shape and curvature including taper in the anterior-posterior direction as well as between the lateral side portions 20 will depend upon the location where the spacer 10 is intended to be inserted.

The upper surface 12, the lower surface 14, or both surfaces 12, 14 of the spacer 10 may include a series or plurality of teeth 26, or other similar projections like rails, fins, or pins, to aid in securing the implant 1 to the vertebral endplates 30, 32. The teeth 26 may be pyramidal in shape as shown or may have other suitable shapes known in the art. The upper and lower surfaces 12, 14 may define a height of the spacer 10, which may range from about 4 to 14 mm, for example. In addition, as shown in FIG. 7, the total length L or depth of the implant 1 including the spacer 10 may range from about 10 to 18 mm, preferably about 12 to 15 mm, and more preferably about 13.5 mm.

The first insertion end portion 16, the second end portion 18 (e.g., back end) opposite the first insertion end portion 16, and the first and second lateral side portions 20 define an outer perimeter of the spacer 10. The shape of the perimeter of the spacer 10 may generally be designed for cervical applications, for example as depicted in FIG. 1, but may also be for the thoracic and lumbar spine. The spacer 10 may have a suitable shape including, but not limited to, an oval, a rectangular box, a trapezoidal box, H-shaped, O-shaped, V-shaped, or the like.

The spacer 10 may be formed from any suitable materials known in the art. For example, the spacer 10 may be comprised of one or more metals, such as stainless steel, titanium and titanium alloys, alloys of cobalt, chromium, and molybdenum (CoCrMo), and other metals and alloys suitable for medical implants; plastics such as polyether ether ketone (PEEK), polyether ketone ketone (PEKK), ultra-high-molecular-weight polyethylene (UHMWPE), carbon fiber reinforced plastics, and other plastics suitable for medical implants; other materials such as ceramics, diamond-like carbon, bone, bone substitutes, and sintered and/or resorbable materials; and combinations of such materials. In addition, the spacer 10 may or may not be coated. For example, a coating may be applied to allow for bone-on or in-growth (e.g., to promote bony fusion or bone growth).

Figure 7:
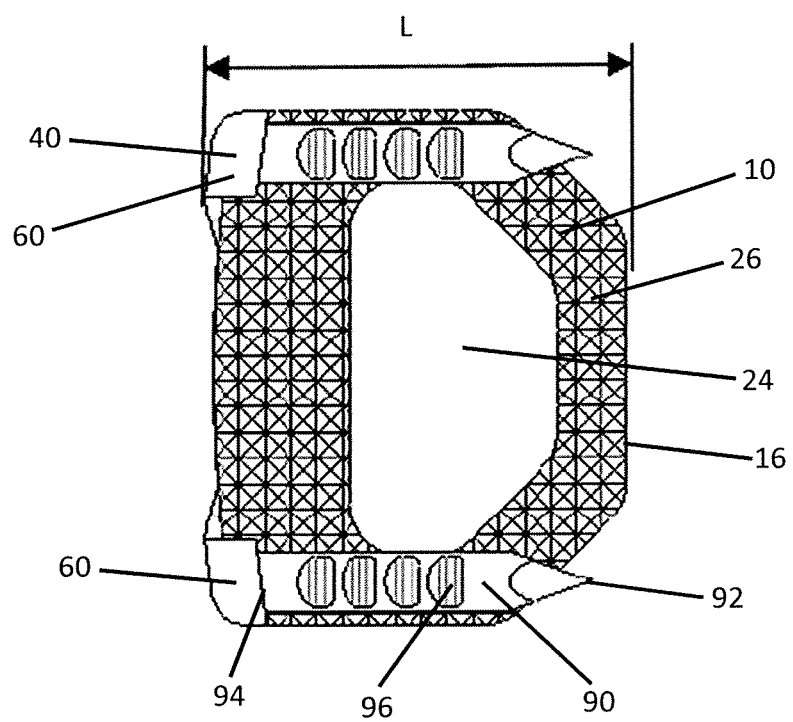
FIG. 7 shows a top view of the implant shown in FIG. 1.

As best seen in FIG. 7, the spacer 10 may include one or more openings 24 suitable for receiving bone (autograft), bone-growth, or graft materials, such as synthetic ceramic (e.g., calcium phosphate), mineralized bone, demineralized bone, collagen, and the like. The one or more openings 24 may extend from the upper surface 12 to the lower surface 14 of the spacer 10 as shown or in any other suitable location through the spacer 10.

The second end portion 18 or back end of the spacer 10, which is positioned opposite to the first insertion end portion 16 of the spacer 10, is coupled to, connected to, or affixed to a fixation frame 40. The spacer 10 may be coupled to the fixation frame 40 using any suitable attachment elements known in the art, such as pins, screws, welds, adhesives, and the like. The connection between the spacer 10 and the fixation frame 40 (and in particular, a bridge portion 42 of the fixation frame) may allow for some degree of relative motion, for example, in order to ease adoption to the anatomy. Thus, the connection between the spacer 10 and the fixation frame 40 may be rigidly or moveably affixed. In one embodiment, the second end portion 18 includes a recess 22 sized and dimensioned to receive at least a portion of the fixation frame 40 (e.g., in a press-fit type arrangement). The bridge portion 42 of the fixation frame 40 may also include one or more cutouts 52 suitable to accommodate pins, screws, or the like. The second end portion 18 may include other openings, bores, or the like (not shown) to further secure the spacer 10 to the fixation frame 40. In another embodiment, the spacer 10 and the fixation frame 40 are comprised of a single contiguous piece of material (e.g., the spacer 10 is molded to the fixation frame 40).

Fixation Frame

Figure 10A:
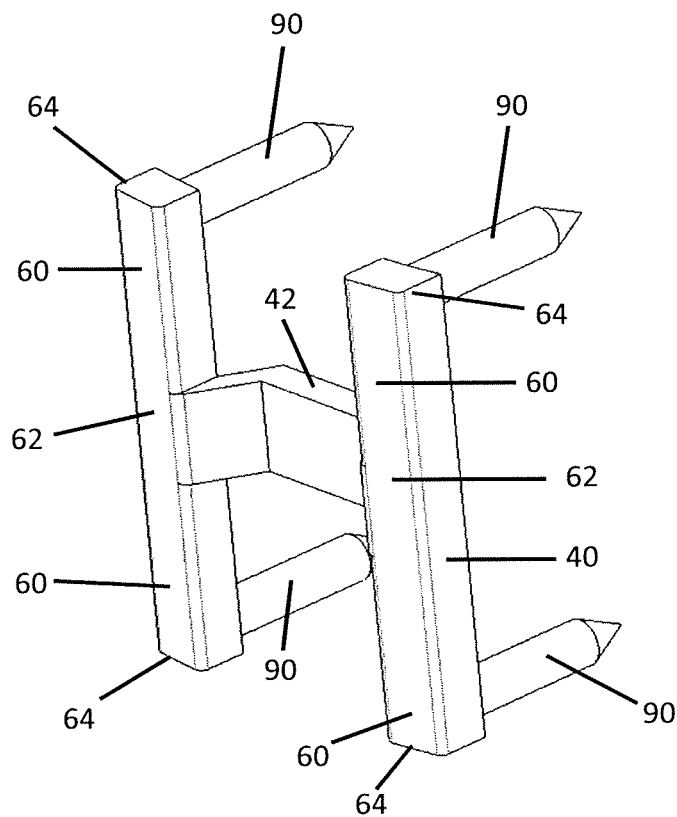
FIGS. 10A and 10B show a perspective view and a top view, respectively, of one embodiment of an H-shaped fixation frame.
Figure 10B:
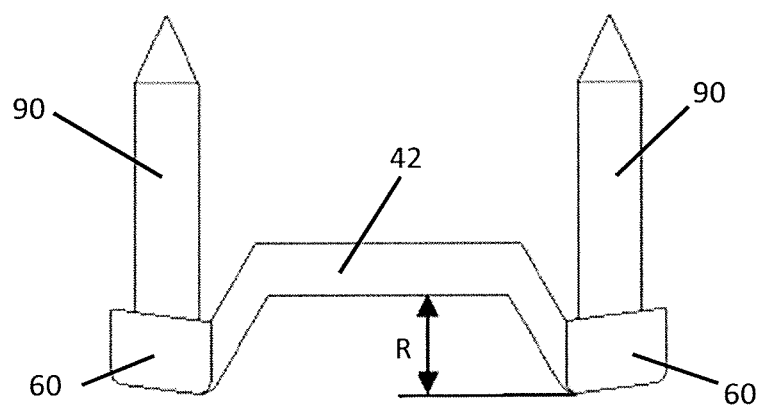

The fixation frame 40 includes the bridge portion 42 and at least one arm 60 extending from the bridge portion 42. The bridge portion 42 may include a first end 44 and a second end 46 (see FIG. 6). Each arm 60 also includes a first end 62 coupled to the bridge portion 42 and a second end 64 extending from the bridge portion (see FIG. 10A). Once implanted between two adjacent vertebral bodies 30, 32, the bridge portion 42 may be oriented substantially coplanar (i.e., in the same plane) with the spacer 10. In particular, the bridge portion 42 may be substantially centrally located with respect to the second end portion 18 of the spacer 10. The second end portion 18 or back end of the spacer 10 may be coupled to the fixation frame 40 using any suitable attachment elements known in the art, such as pins, screws, welds, adhesives, and the like. The bridge portion 42 may also include one or more cutouts 52 suitable to accommodate such attachment element (e.g., pins, screws, or the like).

The one or more arms 60 may extend transversely from the bridge portion 42 or at some angle relative to the bridge portion 42. For example, each of the one or more arms 60 may extend at some angle between about 40 and 90° (e.g., about 45°) relative to the bridge portion 42. In an exemplary embodiment, the one or more of the arms 60 extend transversely from the bridge portion 42 in a perpendicular relationship (e.g., about 90°) relative to the bridge portion 42. Although the arms 60 are preferably provided in a perpendicular relationship from the first and second ends 44, 46 of the bridge portion 42, the arms 60 may be positioned at any suitable location and angle relative to the bridge portion 42 to provide for adequate stabilization of the vertebral bodies 30, 32 and/or to achieve the zero profile design.

The fixation frame 40 may include any suitable number of arms 60, such as two, three, four, or more, to provide stabilization of the vertebral bodies 30, 32. Each of the one or more arms 60 may extend from the bridge portion 42 at any location along the length of the bridge portion 42. For example, the one or more arms 60 may extend from the first end 44, the second end 46, both ends 44, 46, substantially centrally, or at some other location along the length of the bridge portion 42. The one or more arms 60 may extend from the first end 44, the second end 46, or both ends 44, 46 of the bridge portion 42 or may be inset some distance towards the center of the bridge portion 42. For example, in a first direction 80, two arms 60 may extend from the first end 44 and the second end 46, respectively, of the bridge portion 42, and in a second direction 82, one or two arms 60 may extend from the bridge portion 42 inset a distance from the first and/or second ends 44, 46, respectively. As an alternative, a single arm 60 may extend substantially centrally from the bridge portion 42 in either the first or second directions 80, 82.

Figure 6:
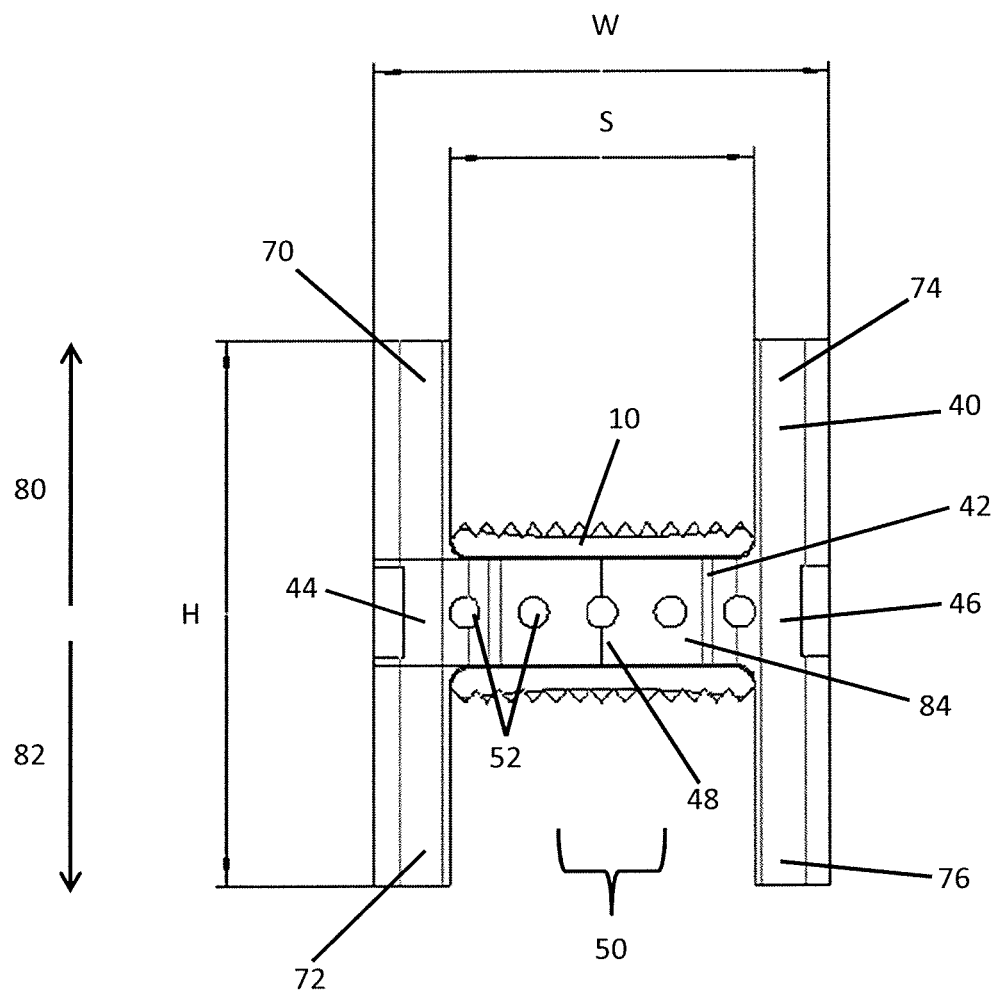
FIG. 6 is an anterior or front view of the implant shown in FIG. 1.

In one embodiment, the fixation frame 40 may be constructed to have an H-shaped configuration. As shown in FIG. 6, a first arm 70 may extend transversely in the first direction 80 from the first end 44 of the bridge portion 42, a second arm 72 may extend transversely in the second direction 82 opposite to the first direction 80 from the first end 44 of the bridge portion 42, a third arm 74 may extend transversely in the first direction 80 from a second end 46 of the bridge portion 42, and a fourth arm 76 may extend transversely in the second direction 82 opposite to the first direction 80 from the second end 46 of the bridge portion 42. Preferably, one or more of the following relationships exist among the arms 60: the first and second arms 70, 72 are coplanar; the third and fourth arms 74, 76 are coplanar; the first and third arms 70, 74 are in parallel; and the second and fourth arms 72, 76 are in parallel.

Each portion of the fixation frame 40 may be separate pieces or may form one single, contiguous piece. For example, the first arm 70 and the second arm 72 may form a single arm portion from the first end 44 of the bridge portion 42. Similarly, the third arm 74 and the fourth arm 76 may form another single arm portion from the second end 46 of the bridge portion 42. In addition, the bridge portion 42 may be separate from or form a continuous piece with one or more of the arms 60. The fixation frame 40 or any portion of the fixation frame 40 may be rigid or flexible in nature.

The fixation frame 40 may also be formed from any suitable material known in the art. For example, the fixation frame 40 may be comprised of one or more metals, such as stainless steel, titanium and titanium alloys, alloys of cobalt, chromium, and molybdenum (CoCrMo), and other metals and alloys suitable for medical implants; plastics such as polyether ether ketone (PEEK), polyether ketone ketone (PEKK), ultra-high-molecular-weight polyethylene (UHM-WPE), carbon fiber reinforced plastics, and other plastics suitable for medical implants; other materials such as ceramics, diamond-like carbon, bone, bone substitutes, and sintered and/or resorbable materials; and combinations of such materials. In addition, the fixation frame 40 may or may not be coated. For example, a coating may be applied to allow for bone-on or in-growth (e.g., to promote bony fusion or bone growth).

The relationship of the at least one arm 60 and the bridge portion 42 may provide for a zero profile implant. For example, the bridge portion 42 may include a center point 48 (or center line when vertically oriented) or center region 50 that is substantially flush with or at least partially recessed from an anterior surface 34 of the superior vertebral body 30, the inferior vertebral body 32, or both vertebral bodies 30, 32 at their respective midlines 36. FIG. 3 shows a cranial-caudal view where the midline 36 defines the center between the lateral sides of the vertebral bodies 30, 32. As is evident, when the spacer 10 and the bridge portion 42 are partially recessed from the anterior surface 34, the implant 1 (specifically, the bridge portion 42 and/or the spacer 10) that sits on the bone does not contact the bone midline 36 at or near the anterior face 34 of the superior and inferior vertebral bodies 30, 32. By not contacting the superior and inferior vertebral bodies 30, 32 in this manner, the risk of esophageal irritation can be reduced or minimized.

Depending on the location of the vertebral bodies 30, 32 and anatomy of the patient, a zero profile implant 1 may be obtained by providing a certain relationship for the arms 60 of the fixation frame 40. As best seen in FIG. 6, a width W of the fixation frame 40 may be determined based on the length of the bridge portion 42 and the position and size of the arms 60. The width W may range from about 10 to 25 mm, preferably about 13 to 20 mm, more preferably about 14 to 16 mm, and even more preferably about 15 mm. The arms 60 may be about 2 to 3 mm in width or about 2.5 mm in width, for example. A spacing S between the arms 60 is determined based on the interior distance between the arms 60. The spacing S may range from about 7 to 15 mm, preferably about 8 to 12 mm, and more preferably about 10 mm. The height H of the implant 1 may be determined by the length of the arms 60 (if necessary, including the height of the bridge portion 42). The length of the arms 60 is preferably at least about 3 mm in order to allow for one or more fixation elements 90 to engage the bone without pulling out or destroying the bone to which the fixation elements 90 are connected. The total height H of the implant 1 may range from about 10 to 25 mm, preferably about 13 to 23 mm, more preferably about 14 to 20 mm, and even more preferably about 16 mm. The height H depends on the height of the spacer 10.

A ratio of the width W of the implant 1 relative to the height H (W/H) of the implant 1 may range from about 0.5 to 1.5, preferably about 0.6 to 1.3, more preferably about 0.7 to 1, and most preferably about 0.8 to 0.9. A ratio of the spacing S of the arms 60 (e.g., a distance between the arms 60) relative to the height H (S/H) of the implant 1 may also be selected. For example, the ratio of the distance S between the arms 60 to the height H (S/H) may range from about 0.3 to 1.2, preferably about 0.5 to 1, and most preferably about 0.5 to 0.6.

Figure 11A:
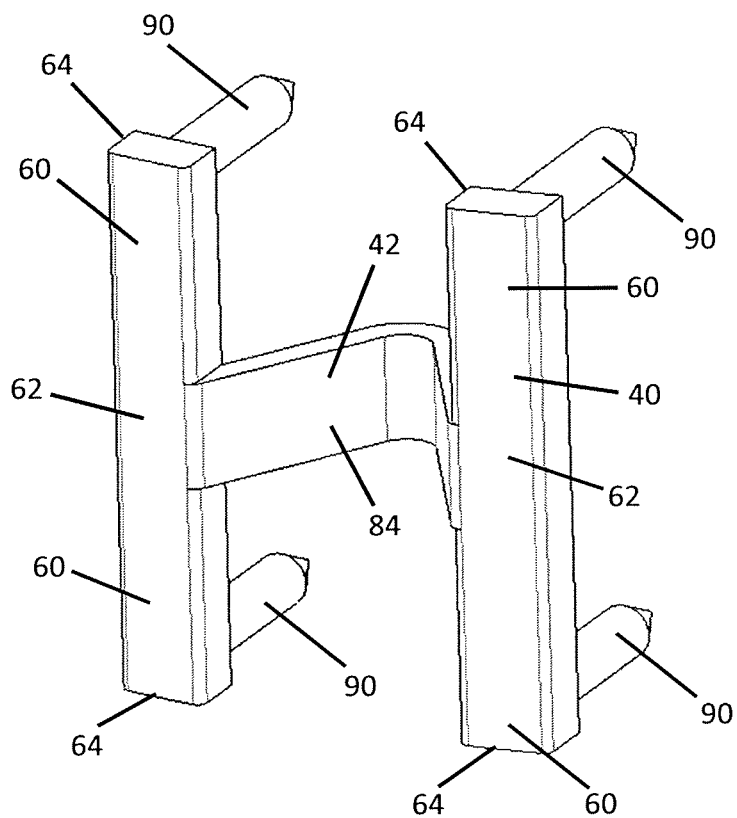
FIGS. 11A and 11B show a perspective view and a top view, respectively, of another embodiment of the H-shaped fixation frame.
Figure 11B:
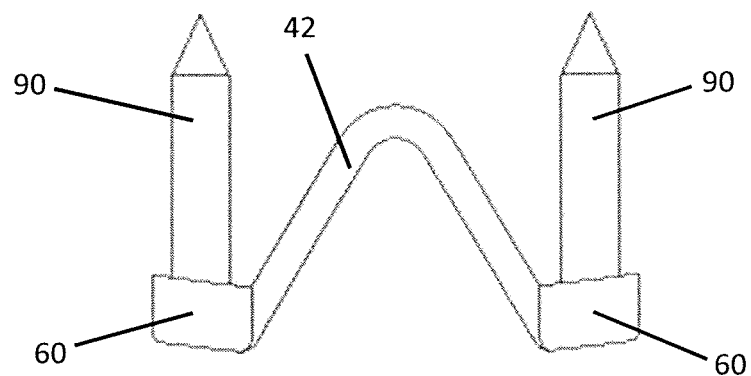
Figure 12A:
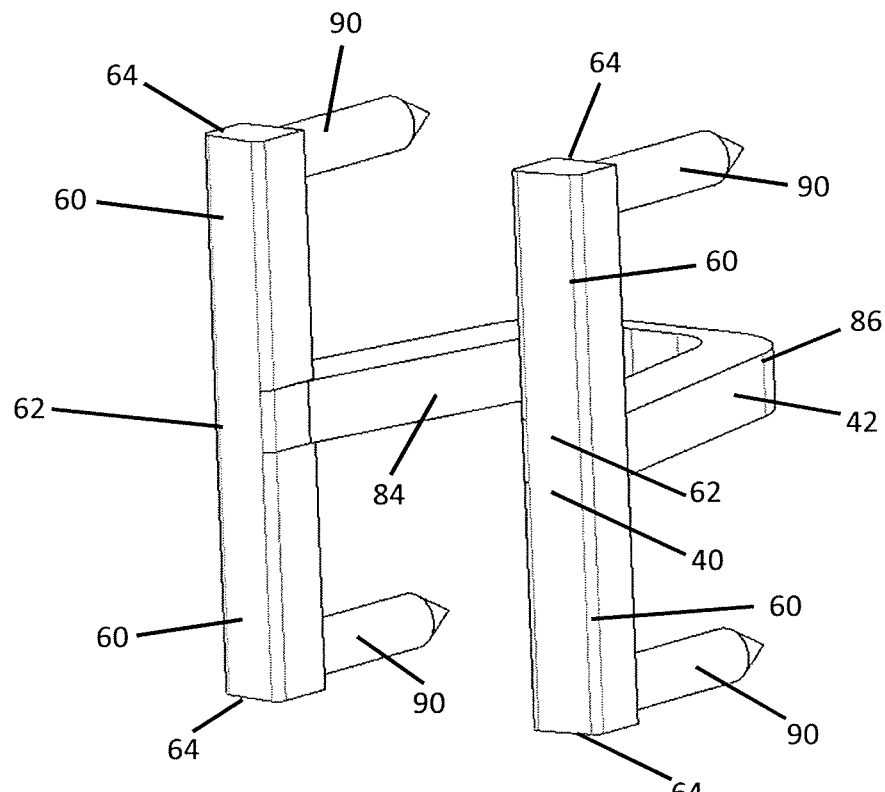
FIGS. 12A and 12B show a perspective view and a top view, respectively, of yet another embodiment of the H-shaped fixation frame.
Figure 12B:
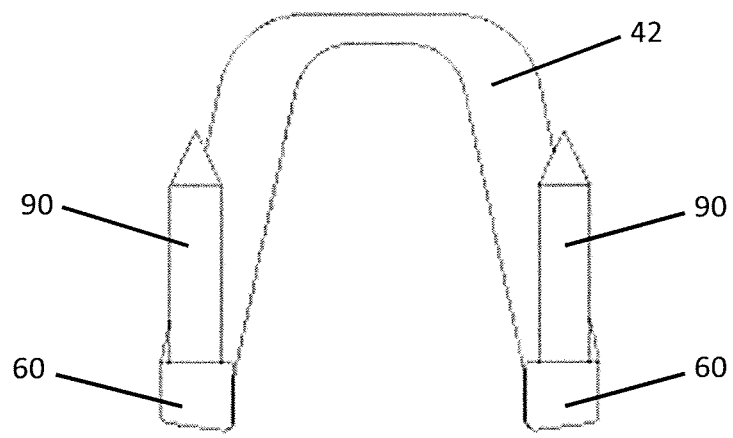

In addition, the bridge portion 42 of the fixation frame 40 may be designed and configured to provide for the zero profile design. The arms 60 may be positioned along a single vertical plane, for example, and at least the central region 50 of the bridge portion 42 may be recessed a distance R (see FIG. 10B) relative to the plurality of arms 60 (e.g., forming a concave portion between the arms 60). The recessed distance R should be selected so as to provide for no contact or minimal contact of the bridge portions 42 on the midline 36 at the anterior face 34 of the vertebral bodies 30, 32. The recessed distance R may range up to about 2 mm (e.g., about 1 to 2 mm), for example. As shown in FIGS. 10A, 10B, 12A, and 12B, the bridge portion 42 may be U-shaped. In the alternative, as shown in FIGS. 11A and 11B, the bridge portion 42 may be V-shaped. The U-shaped or V-shaped configurations may have rounded or sharp corners. The U-shaped or V-shaped design of the bridge portion 42 may also allow for the cavity to be filled with bone (autograft), bone-growth, or graft materials, such as synthetic ceramics (e.g., calcium phosphate), mineralized bone, demineralized bone, collagen, and the like.

Figure 8:
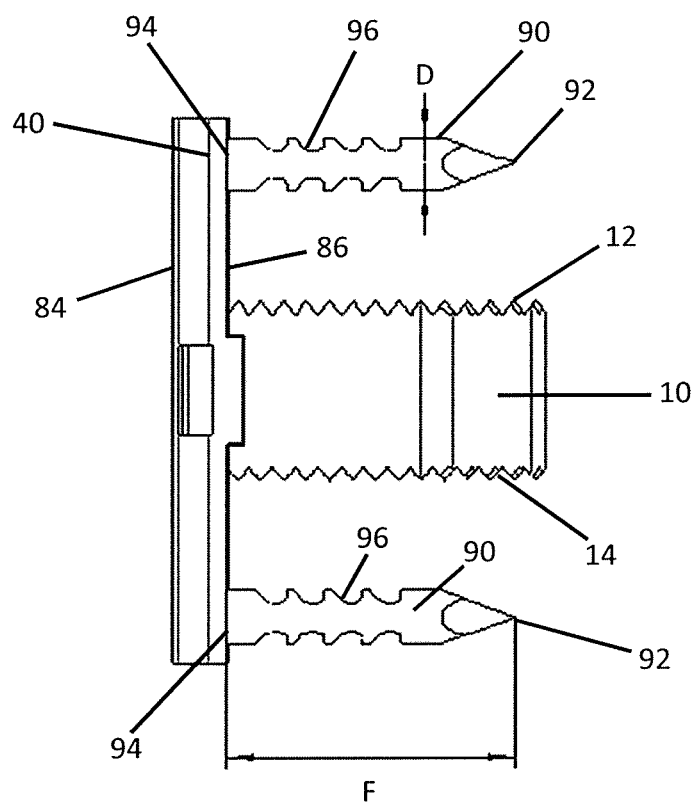
FIG. 8 depicts a lateral or side view of the implant shown in FIG. 1.
Figure 13:
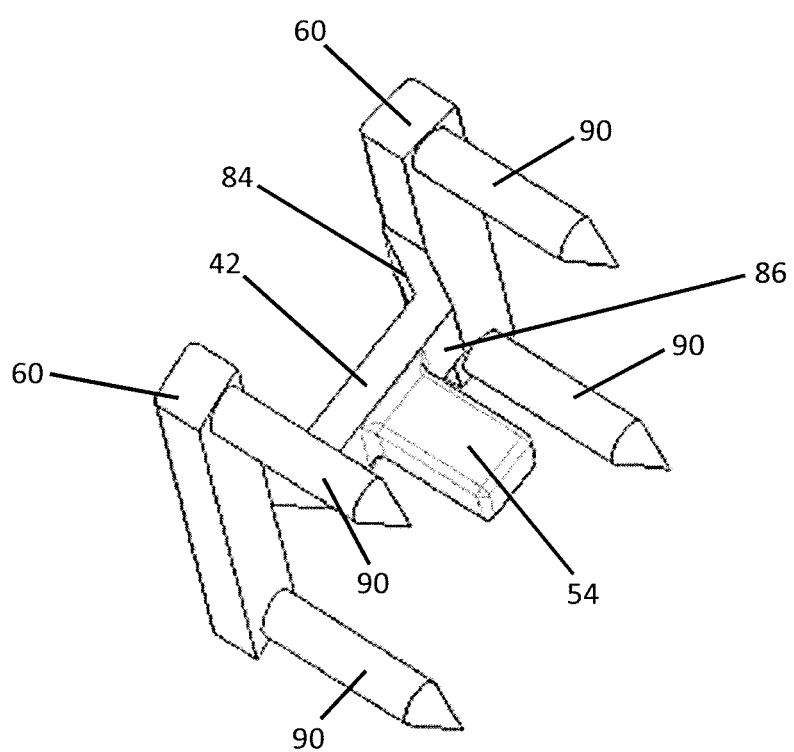
FIG. 13 depicts a perspective view of an embodiment of the H-shaped fixation frame with a central post.

FIG. 8 depicts a lateral or side view of the implant 1 where the fixation frame 40 has a first side 84 and a second side 86. At least a portion of the bridge portion 42 (e.g., at least the second side 86 of the U-shaped or V-shaped portion) may be recessed in the second end portion 18 of the spacer 10 (e.g., in the recess 22 of the spacer 10). In addition, as shown in FIG. 13, the bridge portion 42 may include one or more posts 54 designed to engage with one or more corresponding recesses (not shown) in the spacer 10. For example, as depicted in FIG. 13, the bridge portion 42 may include a single post 54 centrally located on the second side 86 of the bridge portion 42.

The fixation frame 40 may be affixed or coupled to the vertebral bodies 30, 32 using any suitable techniques and equipment known in the art. For example, one or more fixation elements 90 may be used to secure the fixation frame 40 to the vertebral bodies 30, 32. Preferably, the fixation elements 90 are secured to the bone at one or more of the arms 60. In an exemplary embodiment, the fixation elements 90 are positioned transverse and perpendicular to the arms 60, for example, proximate to the second end 64 of each arm 60. Although the fixation elements 90 are depicted in a symmetrical configuration, an asymmetrical configuration (e.g., in different positions along the arm 60 or on alternating arms 60) may also be used.

Figure 9:
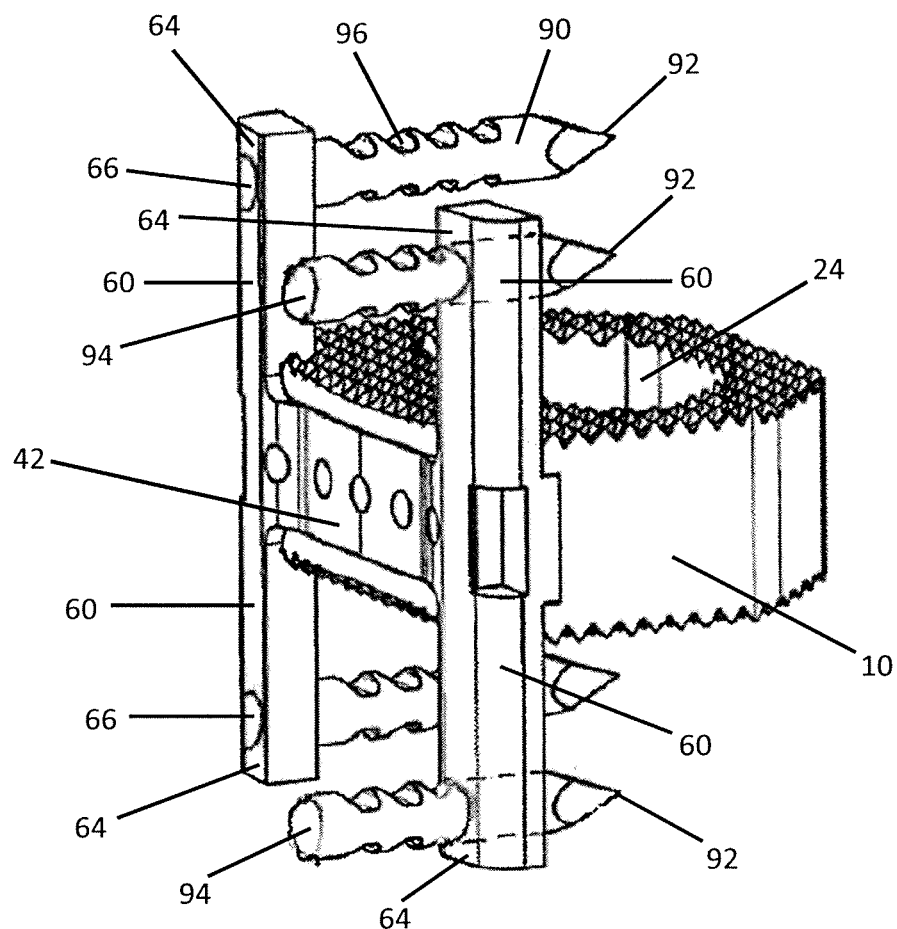
FIG. 9 shows a perspective view of another embodiment of the present invention where the fixation elements may be inserted after the spacer and fixation frame are implanted.

As shown in FIG. 9, the fixation frame 40 (e.g., the arms 60) may include one or more holes 66 that extend from the first side 84 to the second side 86 of the fixation frame 40. The holes 66 may be sized and configured to receive fixation elements 90. The fixation frame 40 may include any suitable type, number, and configuration of through holes 66. The holes 66 may be sized to be approximately equal to the size of the fixation elements 90. Each hole 66 need not have the same configuration or size. The holes 66 may be round in cross-section and dimensioned to allow passage of the fixation element 90 therethrough while resisting passage of the fixation element 90 completely through the hole 66. In some embodiments, at least a portion of the hole 66 can have a non-round cross-section, such as an oval, square, rectangle, polygon or other closed shape. The holes 66 can be provided perpendicularly to the arms 60 or at some angle relative to the arms 60 as the application requires. The fixation elements 90 can be added before, during, or after implantation.

Fixation Element(s)

The fixation elements 90 may be comprised of any suitable fixation elements 90 known in the art. For example, the fixation elements 90 may be selected from pins, blades, staples, screws, bolts, rivets, nails, or the like. The fixation element 90 may include a first insertion end 92 for penetrating the superior or inferior vertebral bodies 30, 32 (e.g., the anterior cortex) and a second end 94, which is coupled to the fixation frame 40. The first end 92 may be blunt or pointed, but is preferably sharp and pointed. The first end 92 of the fixation element 90 may also include an asymmetrical tip or wedge shape.

The fixation elements 90 may be of any suitable size and shape. The fixation elements 90 may vary in both length and width, but generally the length exceeds the width so as to define a generally longitudinal member. The length F of the fixation elements 90 may range from about 6 to 16 mm, for example. Preferably, the length F of the fixation elements 90 is the same or less than the overall length L or depth of the implant 1. The fixation elements 90 may have any suitable cross-section, which may or may not be cannulated and may or may not be perforated. The fixation elements 90 may include a generally spherical cross-section, which may have a diameter D of about 1.2 to 2.5 mm, for example. The fixation elements 90 may be spaced apart a lateral distance (e.g., based on the width W of the fixation frame 40) of about 10 to 17 mm (on centers) and a vertical distance (e.g., based on the height H of the fixation frame 40) of about 12 to 20 mm (on centers).

The fixation elements 90 may also include one or more indentations 96, fins, bumps, knurls, or other features to increase the surface area and/or roughness and improve frictional contact and grip with the vertebral bodies 30, 32. The fixation elements 90 may be formed from any suitable biocompatible materials known in the art, including the types discussed above for the spacer 10 and the fixation frame 40. In a preferred embodiment, the fixation elements 90 are made out of a metal or alloy, which may or may not be coated, as discussed in this document. In addition, the same or different fixation elements 90 may be used at each location (e.g., a pin in one arm 60 and a screw in another arm 60).

In one embodiment, the fixation elements 90 are fastened or affixed (e.g., welded, adhered, etc.) to the fixation frame 40 (in particular, affixed to the second ends 64 of the arms 60) prior to surgery. In other words, the fixation elements 90 are pre-assembled prior to surgery such that the fixation elements 90 are already coupled to the fixation frame 40 at the time of surgery (e.g., during the surgical procedure). For example, the second end 94 of each fixation element 90 may be coupled to the second end 64 of each arm 60 of the fixation frame 40. In the embodiment shown in FIG. 9, the fixation elements 90 may be added during or after implantation, for example, pressed through holes 66 in the arms 60 of the fixation frame 40 after the spacer 10 is placed.

In yet another embodiment, the present invention provides a kit comprising a plurality of implants 1 (in particular, fixation frames 40) of different sizes, dimensions, and/or configurations. For example, the kit may include implants 1 having arms 60 of different lengths and varying distances between the arms 60 suitable for the vertebral body to be operated on (e.g., different patient anatomies) and to achieve the zero profile design. In particular, different ratios of the width W to the height H (W/H) and spacing S of the arms 60 relative to the height H (S/H) may be provided.

Preferred embodiments of the present invention are directed to applications in the spine for anterior stabilization. In particular, the implant 1 may be suitable for application in the cervical spine, as well as the thoracic and lumbar spine.

The preferred embodiments are not limited to applications or mounting in the anterior spine, however, and may be utilized for other approaches to the spine (e.g., sagittal plane) or for mounting to other bones in the human body, as would be apparent to one having ordinary skill in the art.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. An implant for insertion into an intervertebral disc space between superior and inferior vertebral bodies wherein the superior and inferior vertebral bodies include an anterior surface and a midline extending therealong, the implant comprising:
   a spacer including an upper surface for contacting the superior vertebral body, a lower surface for contacting the inferior vertebral body, a first insertion end portion, and a second end portion opposite the first insertion end portion;
   a fixation frame coupled to the second end portion of the spacer, the fixation frame including a bridge portion oriented substantially coplanar with the spacer and at least one arm extending from the bridge portion; and
   at least one fixation element having a first insertion end for penetrating the superior or inferior vertebral bodies and a second end coupled to the at least one arm of the fixation frame;
   wherein the bridge portion is shaped along its length such that a central region of the bridge portion is recessed from first and second lateral ends of the bridge portion and such that the central region is recessed from the second end portion of the spacer; and
   wherein the at least one arm is positioned along a first plane and at least the central region of the bridge portion is recessed relative to the at least one arm.

2. The implant of claim 1, wherein the bridge portion includes a first end and a second end and the at least one arm comprises four arms, a first arm extends transversely in a first direction from the first end of the bridge portion, a second arm extends transversely in a second direction opposite to the first direction from the first end of the bridge portion, a third arm extends transversely in the first direction from the second end of the bridge portion, and a fourth arm extends transversely in the second direction opposite to the first direction from the second end of the bridge portion.

3. The implant of claim 1, wherein the fixation frame comprises an H-shaped configuration.

4. The implant of claim 1, wherein the fixation frame has a first side and a second side, and at least one through hole sized and adapted for receiving the fixation element extends through the first side to the second side of the fixation frame.

5. The device of claim 1, wherein the at least one arm has a length of at least about 3 mm.

6. The device of claim 1, wherein the bridge portion is substantially rectangular shaped.

7. An implant for insertion into an intervertebral disc space between superior and inferior vertebral bodies, the implant comprising:

a spacer including an upper surface for contacting the superior vertebral body, a lower surface for contacting the inferior vertebral body, a first insertion end portion, and a second end portion opposite the first insertion end portion;

an H-shaped fixation frame including a bridge portion having a first lateral end and a second lateral end and a plurality of arms each having a first end coupled to the bridge portion and a second end extending from the bridge portion, wherein the bridge portion is coupled to the second end portion of the spacer, the plurality of arms include a first arm extending transversely in a first direction from the first end of the bridge portion, a second arm extending transversely in a second direction opposite to the first direction from the first end of the bridge portion, a third arm extending transversely in the first direction from the second end of the bridge portion, and a fourth arm extending transversely in the second direction opposite to the first direction from the second end of the bridge portion; and a plurality of fixation elements each having a first insertion end for penetrating the superior or inferior vertebral bodies and a second end coupled proximate to the second end of each of the arms of the fixation frame;

wherein the first, second, third, and fourth arms are positioned along a single vertical plane; and wherein the bridge portion is U-shaped or V-shaped along its length such that a central region of the bridge portion is recessed from the first and second lateral ends of the bridge portion and such that the central region is recessed from the second end portion of the spacer.

8. The implant of claim 7, wherein the plurality of arms define a maximum height of the implant and a width of the implant, and a ratio of the width to the height ranges from about 0.5 to 1.5.

9. The implant of claim 7, wherein the plurality of arms define a maximum height of the implant and wherein the first arm and the third arm are spaced a distance apart and the second arm and the fourth arm are spaced the same distance apart, and a ratio of the distance between the arms and the height ranges from about 0.3 to 1.2.

10. The implant of claim 7, wherein the superior and inferior vertebral bodies include an anterior surface and a midline, and the bridge portion does not contact the superior or inferior vertebral bodies at the midline proximate to the anterior surface providing a zero profile once implanted.

11. The implant of claim 7, wherein the bridge portion or the spacer is adapted to receive and contain at least one bone growth or graft material.

12. The implant of claim 7, wherein the second end portion of the spacer comprises a recess sized and configured to receive at least a portion of the bridge portion of the fixation frame.

13. The implant of claim 7, wherein the bridge portion comprises a post and the second end portion of the spacer includes an opening sized to receive the post.

14. The implant of claim 7, wherein the plurality of fixation elements are permanently affixed to the plurality of arms of the fixation frame prior to and following implantation into a vertebra.

15. The implant of claim 7, wherein each arm comprises at least one through hole sized and configured for receiving one of the plurality of fixation elements suitable for coupling the fixation frame to the superior or inferior vertebral bodies.

16. The implant of claim 7, wherein the plurality of fixation elements are selected from the group consisting of screws, pins, blades, and staples.

17. The implant of claim 7, wherein the spacer and the fixation frame form a single contiguous piece of material.

18. The device of claim 17, wherein the H-shaped fixation frame is molded to the spacer.

19. The implant of claim 7, wherein the upper surface, the lower surface, or both surfaces of the spacer comprise a plurality of teeth or projections.

20. A kit comprising a plurality of implants in accordance with claim 7 of different sizes, shapes or dimensions.

21. The device of claim 7, wherein the first, second, third, and fourth arms each have a length of at least about 3 mm.

22. The device of claim 7, wherein the central region of the bridge portion is recessed by a distance of 1 to 2 mm relative to the first and second lateral ends of the bridge portion.

* * * * *